United States Patent [19]

Schreyer et al.

[11] 4,052,445

[45] Oct. 4, 1977

[54] PROCESS FOR THE PRODUCTION OF ALKYL SULFONIC ACIDS

[75] Inventors: Gerd Schreyer; Friedhelm Geiger; Jorg Hensel, all of Hanau, Germany

[73] Assignee: Deutsch Gold- und Silber-Scheideanstalt Vormals Roessler, Frankfurt, Germany

[21] Appl. No.: 655,018

[22] Filed: Feb. 4, 1976

Related U.S. Application Data

[63] Continuation-in-part of Ser. No. 654,062, Feb. 2, 1976, abandoned.

[30] Foreign Application Priority Data

Feb. 1, 1975  Germany .............................. 2504201

[51] Int. Cl.$^2$ .......................................... C07C 143/02

[52] U.S. Cl. ................................................ 260/513 R
[58] Field of Search .................................... 260/513 R

[56] References Cited

U.S. PATENT DOCUMENTS 3,670,002   6/1972   Sheng et al. ..................... 260/513 R Primary Examiner—James O. Thomas, Jr.
Assistant Examiner—Nicky Chan
Attorney, Agent, or Firm—Cushman, Darby & Cushman

[57] ABSTRACT

Alkylsulfonic acids are prepared by oxidation of an alkyl mercaptan or dialkyl disulfide with hydrogen peroxide in an inert medium in the presence of ammonium or alkali molybdate or ammonium or alkali tungstate.

13 Claims, No Drawings

PROCESS FOR THE PRODUCTION OF ALKYL SULFONIC ACIDS

This application is a continutation-in-part of application Ser. No. 654,062, filed Feb. 2, 1976 and now abandoned.

The present invention is directed to a process for the product of alkyl sulfonic acids by the oxidation of alkyl mercaptans or dialkyl disulfides.

Alkylsulfonic acids (also called alkanesulfonic acids) are of interest as strong, non-oxidizing acids, both as solvents and also as catalysts in alkylation, esterification and polymerization reactions.

Various processes are known for producing alkylsulfonic acids. Thus Koenig U.S. Pat. No. 2,892,852 describes the oxidation of organic thioethers and thioacetic acid esters with peracetic acid in acetic acid.

An oxidation of thiolacetates with performic acid also is known, see *H. Nawa et al., J. Amer. Chem. Soc.* 82, 896 (1960).

Still more expensive than the described processes are processes using ozone as the oxidizing agent, see *J. Praktische Chemie* (4), 2, 241 (1955).

Likewise, processes involving the electrolytic oxidation of methyl mercaptan can be carried out with difficulty, see Johnson U.S. Pat. No. 2,727,920. There is also described in that patent the reaction of mercaptans with nitric acid, which, however, cannot be employed for large scale processes because of the, in a given case, explosive-like acceleration of the reaction velocity.

Additionally, according to a process described in J. Org. Chem. Vol. 27, pages 2853 et seq. (1962) sulfonic acids are produced by the oxidation of thio compounds with in situ formed peracetic acid. This process is also very expensive.

The invention is based on the problem of developing a process for the production of alkylsulfonic acids which gives high yields of alkylsulfonic acids in an inexpensive manner.

The objects of the invention are accomplished by developing a process for the production of alkylsulfonic acids by oxidation of an alkyl mercaptan or dialkyl disulfide with hydrogen peroxide in an inert medium in the present of ammonium or alkali molybdate or ammonium or alkali tungstate. Thus, there can be used sodium tungstate, potassium tungstate, sodium molybdate and potassium molybdate.

As alkyl mercaptans, there can be employed, for example, those having 1-18, preferably 1-6 carbon atoms. Thus, there can be used methyl mercaptan, ethyl mercaptan, propyl mercaptan, isopropyl mercaptan, butyl mercaptan, amyl mercaptan, sec. butyl mercaptan, hexyl mercaptan, octyl mercaptan, hexadecyl mercaptan, octadecyl mercaptan or decyl mercaptan. As dialkyl disulfides there are used, for example, compounds having 2-20, preferably 2-12 carbon atoms. Thus, there can be used dimethyl disulfide, diethyl disulfide, dipropyl disulfide, diisopropyl disulfide, dibutyl disulfide, diamyl disulfide, dihexyl disulfide, dioctyl disulfide or didecyl disulfide.

The rection can be carried out in water as a chemically inert medium. Thereby there is suitably dropped hydrogen peroxide dissolved in water into the alkyl mercaptan or dialkyl disulfide present in an aqueous medium in the presence of ammonia or alkali metal molybdate or ammonia or alkali metal tungstate.

The concentration of the aqueous hydrogen peroxide solutions are not critical. Thus, there are suitable the commercial solutions with a concentration of hydrogen peroxide of 25-70 weight %, but there are also suitable hydrogen peroxide concentrations up to 90 weight %. Lower concentrations of hydrogen peroxide can also be used, down to 3 weight %. Preferably there are used solutions with a concentration of 10 to 50 weight % of hydrogen peroxide.

The amount of solvent is not critical but, in carrying out the reaction of the invention, preferably there is employed an at least 5 fold molar amount of water based on the amount of alkyl mercaptan or dialkyl disulfide used. The water can be used, for example, in a molar amount of 5 to 20 moles per mole of alkyl mercaptan or dialkyl disulfide.

This ratio of water to starting compound should be present at the beginning of the reaction whereupon in the portionwise addition of the aqueous hydrogen peroxide solution depending on the concentration of the added solution there is more or less of a shifting to a larger amount of water.

Furthermore, the reaction of the invention is carried out in the presence of $10^{-2}$ up to 1 mol % of ammonium or alkali metal molybdate or ammonium or alkali metal tungstate based on the alkyl mercaptan or dialkyl disulfide employed.

The material to be oxidized, i.e., the alkyl mercaptan or dialkyl disulfide, and the hydrogen peroxide can be employed in equivalent amounts, although an excess of either reactant can be employed, first of all, the hydrogen peroxide.

The temperatures at which the process of the invention is carried out depends on the manner of carrying out the process. If a mixture of alkyl mercaptan or dialkyl disulfide cooled below its boiling point with ammonium or alkali metal molybdate or ammonium or alkali metal tungstate, in a given case, dissolved in water or another solvent, is employed and then hydrogen peroxide added, attention must be paid that there is excluded a temperature increase above the boiling point of the reaction mixture during the addition of the first-third of the equivalent amount of hydrogen peroxide. With too quick an increase in temperatue, the heat of rection can not longer be drawn off and the rection held under control.

During the addition of the last two-thirds of the equivalent amount of hydrogen peroxide, the temperatue of the mixture can increase to the boiling point, i.e., the speed of inflow of hydrogen peroxide is increased in comparison to the first phase of the reaction.

According to another variant of the process, the hydrogen peroxide solution and the ammonium or alkali metal molybdate or ammonium or alkali metal tungstate is present as a mixture and then the sulfur-containing compound is fed in.

By heating the reaction is started and by cooling and corresponding regulation of the speed of dosing the sulfur-containing compound, the reaction mixture is held at the boiling temperature and, thus, carried to completion.

In continuous carrying out of the process, it is recommended to carry out the reaction in two steps. Hereby the reaction is started according to one of the variants named above in a main reaction vessel and the reactants are added preferably in stoichiometrical amounts. The reaction is carried to completion in a subsequent reactor.

To work up the reaction product, after removing excess hydrogen peroxide first the greatest part of the water can be distilled off and then the alkylsulfonic acid separated from the solid portion in a Sambay evaporator.

Then the purification distillation of the alkylsulfonic acid can take place under reduced pressure. Hereby there is readily produced a nearly 100% product.

Unless otherwise indicated all parts and percentages are by weight.

The process of the invention is explained further by the following examples.

EXAMPLE 1

(According to the State of the Art)

There were dropped into 48 grams of methyl mercaptan in 100 grams of water with stirring in the course of 3 hours 3 moles of hydrogen peroxide in a total of 294 ml of aqueous solution. Subsequently, the reaction mixture was held for one hour at the boiling temperatue.

No reaction of the methyl mercaptan with the hydrogen peroxide took place.

EXAMPLE 2

(According to the Invention)

There were added to 48 grams of methyl mercaptan and 7.5 grams ($6.3 \times 10^{-3}$ moles) of ammonium para molybdate in 100 grams of water in the course of 3 hours 3 moles of hydrogen peroxide in a total of 294 ml of aqueous solution.

The reaction temperature increased from 10° C. to 90° C. At the completion of the reaction, the reaction mixture was held to 100° to 110° C. The hydrogen peroxide added was completely reacted.

The working up of the reaction product gave a 85.5% yield of pure methanesulfonic acid.

The process can comprise, consist essentially of, or consist of the steps set forth using the stated materials.

What is claimed is

1. A process for the production of an alkylsulfonic acid comprising oxidizing an alkyl mercaptan or a dialkyl disulfide with hydrogen peroxide in an inert medium in the presence of ammonium molybdate, alkali metal molydbate, ammonium tungstate or alkali metal tungstate.

2. The process of claim 1 wherein the alkyl mercaptan has 1 to 18 carbon atoms and the dialkyl disulfide has 2 to 20 carbon atoms.

3. The process of claim 2 wherein the alkyl mercaptan has 1 to 6 carbon atoms and the dialkyl disulfide has 2 to 12 carbon atoms.

4. The process of claim 3 wherein there is employed methyl mercaptan.

5. The process of claim 1 wherein the reaction is carried out in water.

6. The process of claim 5 wherein there is employed an at least 5-fold molar amount of water based on the amount of alkyl mercaptan or dialkyl disulfide employed.

7. The process of claim 6 wherein there is employed $10^{-2}$ to 1 mol % of ammonium molybdate, alkali metal molybdate, ammonium tungstate or alkali metal tungstate based on the amount of alkyl mercaptan or dialkyl disulfide employed.

8. The process of claim 1 where there is employed $10^{-2}$ to 1 mol % of the ammonium molybdate, alkali metal molybdate, ammonium tungstate or alkali metal tungstate.

9. The process of claim 2 wherein the reaction is carried out in water.

10. The process of claim 9 wherein there is employed an at least 5-fold molar amount of water based on the amount of alkyl mercaptan or dialkyl disulfide employed.

11. The process of claim 10 wherein there is employed $10^{-2}$ to 1 mol % of ammonium molybdate, alkali metal molybdate, ammonium tungstate or alkali metal tungstate based on the amount of alkyl mercaptan or dialkyl disulfide.

12. The process of claim 11 wherein there is employed an alkyl mercaptan having 1 to 6 carbon atoms in the alkyl group.

13. The process of claim 11 wherein there is employed a dialkyl disulfide having 2 to 12 carbon atoms.

* * * * *